United States Patent
Jiang et al.

(10) Patent No.: US 12,329,924 B2
(45) Date of Patent: Jun. 17, 2025

(54) UNIVERSAL SINGLE-USE CAP FOR MALE AND FEMALE CONNECTORS

(71) Applicant: Becton, Dickinson and Company, Franklin Lakes, NJ (US)

(72) Inventors: Chang Jiang, Butler, NJ (US); Nichola Charles, Budd Lake, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 911 days.

(21) Appl. No.: 17/045,840

(22) PCT Filed: Apr. 9, 2019

(86) PCT No.: PCT/US2019/026536
§ 371 (c)(1),
(2) Date: Oct. 7, 2020

(87) PCT Pub. No.: WO2019/199788
PCT Pub. Date: Oct. 17, 2019

(65) Prior Publication Data
US 2021/0138223 A1 May 13, 2021

Related U.S. Application Data

(60) Provisional application No. 62/655,512, filed on Apr. 10, 2018.

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01); *A61M 2205/02* (2013.01)

(58) Field of Classification Search
CPC ................ A61M 39/18; A61M 39/162; A61M 2205/02; A61M 39/20; A61M 2039/0686;
(Continued)

(56) References Cited

U.S. PATENT DOCUMENTS 4,440,207 A * 4/1984 Genatempo ............. A61L 31/16
604/905
2010/0106102 A1 4/2010 Ziebol et al.
(Continued)

FOREIGN PATENT DOCUMENTS

CN 106824886 A 6/2017
CN 107198822 A 9/2017
(Continued)

OTHER PUBLICATIONS

PCT International Search Report and Written Opinion in PCT/US2019/026536 dated Jul. 2, 2019, 14 pages.

*Primary Examiner* — Courtney B Fredrickson
*Assistant Examiner* — Kayla M. Turkowski
(74) *Attorney, Agent, or Firm* — SERVILLA WHITNEY LLC

(57) ABSTRACT

A device for connection to a medical connector, the device includes a cap having an annular wall having an exterior wall surface and an interior wall surface including a plurality of inwardly extending protrusions sized and shaped to frictionally engage a male luer, and a peelable seal. The cap configured to define a chamber to contain an absorbent material and disinfectant or antimicrobial agent. The cap includes one or more threads adapted to engage with a female luer connector. The cap is adapted to engage a male luer connector in a press-fit connection. The peelable seal prevents the disinfectant or the antimicrobial agent from exiting the chamber. Also described are methods of disinfecting a medical connector, and apparatuses comprising a device for disinfecting a medical connector.

18 Claims, 10 Drawing Sheets

(58) Field of Classification Search
CPC ... A61M 39/16; A61B 90/70; A61L 2300/404
See application file for complete search history.

(56) References Cited

U.S. PATENT DOCUMENTS

| | | |
|---|---|---|
| 2011/0044850 A1 | 2/2011 | Solomon et al. |
| 2012/0220955 A1* | 8/2012 | Maseda ................ A61M 39/20 |
| | | 604/256 |
| 2013/0006194 A1 | 1/2013 | Anderson et al. |
| 2015/0086441 A1* | 3/2015 | She ......................... A61L 2/18 |
| | | 422/294 |
| 2016/0045629 A1* | 2/2016 | Gardner ................ A61B 90/70 |
| | | 422/292 |
| 2016/0185514 A1 | 6/2016 | Tennican et al. |
| 2017/0203092 A1 | 7/2017 | Ryan et al. |
| 2017/0232121 A1* | 8/2017 | Chiu ........................ B08B 3/04 |
| | | 422/28 |
| 2018/0071508 A1 | 3/2018 | Drmanovic |

FOREIGN PATENT DOCUMENTS

| | | |
|---|---|---|
| EP | 1977714 B1 | 1/2019 |
| WO | 2015174953 A1 | 11/2015 |

* cited by examiner

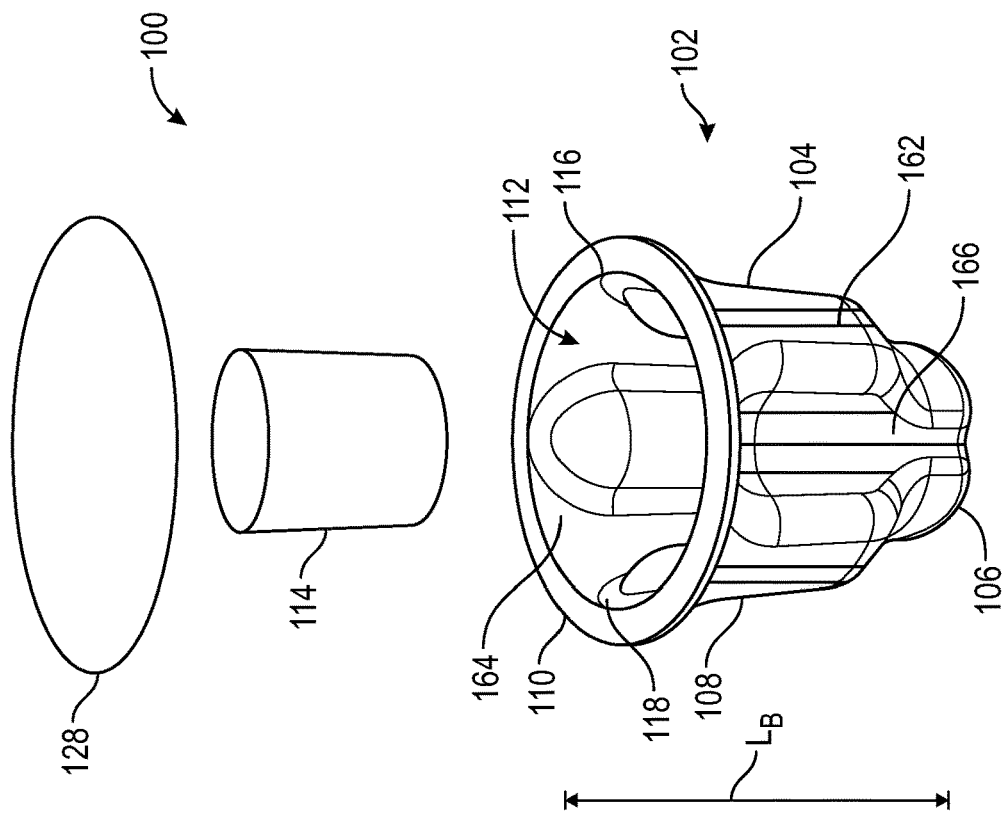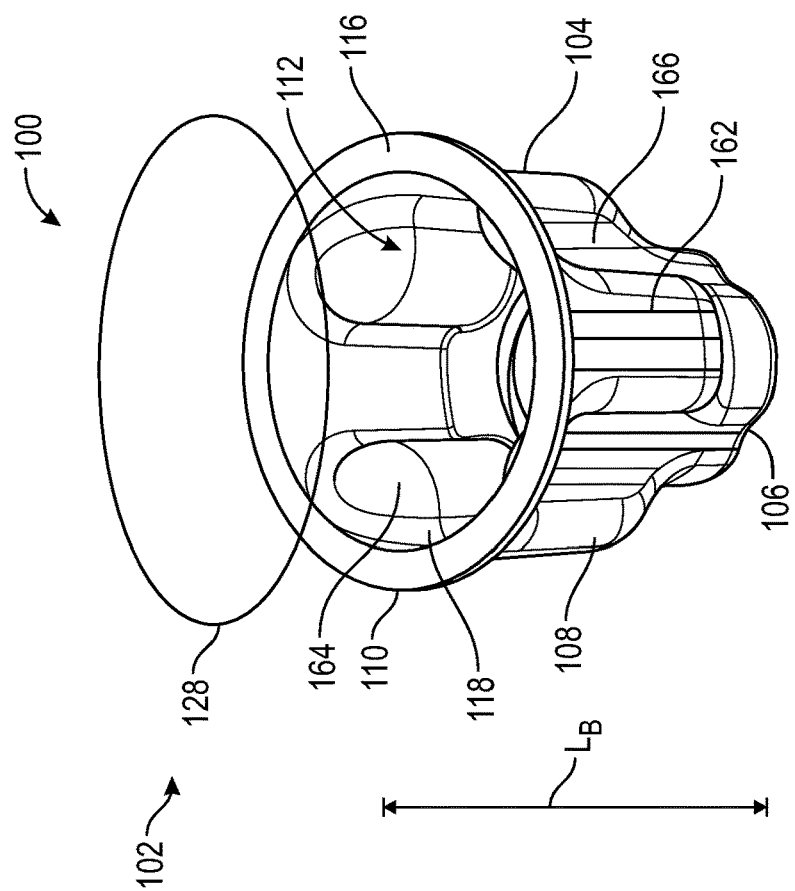

UNIVERSAL SINGLE-USE CAP FOR MALE AND FEMALE CONNECTORS

CROSS-REFERENCE TO RELATED APPLICATIONS

This application is the national stage entry of PCT/US2019/026536, filed on Apr. 9, 2019, which claims priority from provisional U.S. Patent Application No. 62/655,512 filed Apr. 10, 2018, the disclosures of which are hereby incorporated by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are therefore limited to the types of connectors to which the cap can be attached. Thus, prior disinfecting caps were designed to fit one type of connector only, and were specific to one particular size and/or shape of connector. Thus, there is a need for a disinfecting device capable of accommodating multiple types of connectors to streamline the disinfecting process. There is also a need for a disinfecting device capable of continuous disinfection for multiple days.

SUMMARY

One aspect of the present disclosure pertains to device for connection to a medical connector according to an exemplary embodiment of the present disclosure generally comprises a cap, absorbent material, a disinfectant or the antimicrobial agent and a peelable seal. The cap comprises an integral body, a closed end, an annular wall having a length extending from the closed end to an open end that defines a chamber containing an absorbent material and disinfectant or antimicrobial agent. The open end defines an end face and an engagement surface.

The annular wall of the cap comprises an exterior wall surface and an interior wall surface. The interior wall surface comprises a plurality of inwardly extending protrusions sized and shaped to frictionally engage a male luer connector. The interior wall surface also comprises internal threads adjacent the closed end. The internal threads are adapted and sized to engage a female luer connector.

In one or more embodiments, the plurality of inwardly extending protrusions are sized to define an opening having a diameter that is dilatable from an initial diameter of from about 7-9 mm to a dilated diameter of about 9-12 mm to accept a collar of a male connectors. In one or more embodiments, the male luer connector frictionally engages the inwardly extending protrusions opening via a press-fit connection upon insertion into the chamber.

In one or more embodiments, the plurality of inwardly extending protrusions extends along an entire length of the interior wall surface of the cap. In yet another embodiment, the plurality of inwardly extending partially extends along the length of the interior wall surface of the cap.

In one or more embodiments, the plurality of inwardly extending protrusions is elongate. In one or more embodiments, the plurality of inwardly extending protrusions is tapered.

In one or more embodiments, the opening adjacent the open end of the interior wall surface is sized and adapted to receive a male luer connector in a press-fit connection.

The interior wall surface comprises internal threads adjacent to the closed end. The internal threads are adapted and sized to engage a female luer connector. In one or more embodiments, the internal threads adjacent the closed end of the cap partially extend along a length of the interior wall surface of the cap.

The absorbent material and the disinfectant or the antimicrobial agent contacts the male luer connector, the female luer connector and the hemodialysis connector after insertion of the connector through the dilatable opening.

The peelable seal is disposed on the end face of the cap to prevent the disinfectant or the antimicrobial agent from exiting the chamber.

In one or more embodiments, the female luer connector is selected from the group consisting of needle-free connectors, stopcocks, and hemodialysis connectors.

In one or more embodiments, the male connector is an intravenous tubing end or stopcock.

In one or more embodiments, the male luer connector rests on the peripheral ledge upon being fully inserted in into the chamber.

In one or more embodiments, the chamber comprises a first portion adjacent the closed end having a first portion diameter and a second portion adjacent the open end having a second portion diameter, the first portion and second portion in fluid communication with each other and the first portion diameter being less than the second portion diameter. In one or more embodiments, the annular wall of the cap is frusto-conically shaped.

In one or more embodiments, the cap comprises a polypropylene or polyethylene material. In one or more embodiments, the exterior cap surface includes a plurality of grip members.

In one or more embodiments, the absorbent material is under radial compression by the internal threads to retain the absorbent material in the chamber. In one or more embodiments, the absorbent material is retained within the chamber without being radially compressed from the internal threads. In one or more embodiments, the absorbent material is a nonwoven material, foam or a sponge. In a specific embodiment, the foam is a polyurethane foam.

In one or more embodiments, the cap comprises a polypropylene or polyethylene material.

In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material toward the closed end of the chamber upon connection to the female luer connector or the male luer connector allows the connector to contact the disinfectant or antimicrobial agent to disinfect the female luer connector or the male luer connector. When a male luer connector, a female luer connector or hemodialysis connector is inserted through the open end, the absorbent material and the disinfectant or the antimicrobial agent contact the male luer connector, female luer connector or hemodialysis connector.

In one or more embodiments, the cap further comprises a peripheral ledge extending radially inward from the annular wall.

In one or more embodiments, the peelable seal comprises an aluminum or multi-layer polymer film peel back top. In a specific embodiment, the peelable seal is heat-sealed or induction sealed to the cap open end.

A second aspect of the present disclosure pertains to methods of disinfecting medical connectors. In one or more embodiments, a method of disinfecting a medical connector comprises connecting the device of one or more embodiments to a medical connector, wherein connecting includes frictionally engaging the interior wall surface upon insertion into the chamber or engaging the internal threads, such that the medical connector contacts the absorbent material and the disinfectant or antimicrobial agent.

A third aspect of the present disclosure pertains to an assembly. The assembly comprises the device of one or more embodiments connected to a medical connector. In one or more embodiments, the medical connector is selected from a male luer connector, a female luer connector, and needleless connector.

BRIEF DESCRIPTION OF THE DRAWINGS

FIG. 1 shows a top perspective view of an embodiment of a device of the present disclosure;

FIG. 2 shows a top perspective elevation view of an embodiment of a device of the present disclosure;

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Embodiments of the disclosure pertain to a universal single-use device for connection to and disinfection of a medical connector, including male luer connectors and female luer connectors, in which the device comprises a cap, absorbent material, a disinfectant or the antimicrobial agent and a peelable seal. Embodiments of the disclosure pertain to a device that provides a mechanical barrier for connectors and contains an antimicrobial agent for disinfection. Embodiments of the disclosure pertain to a device that allows a practitioner to streamline the disinfecting process.

Figure 3:
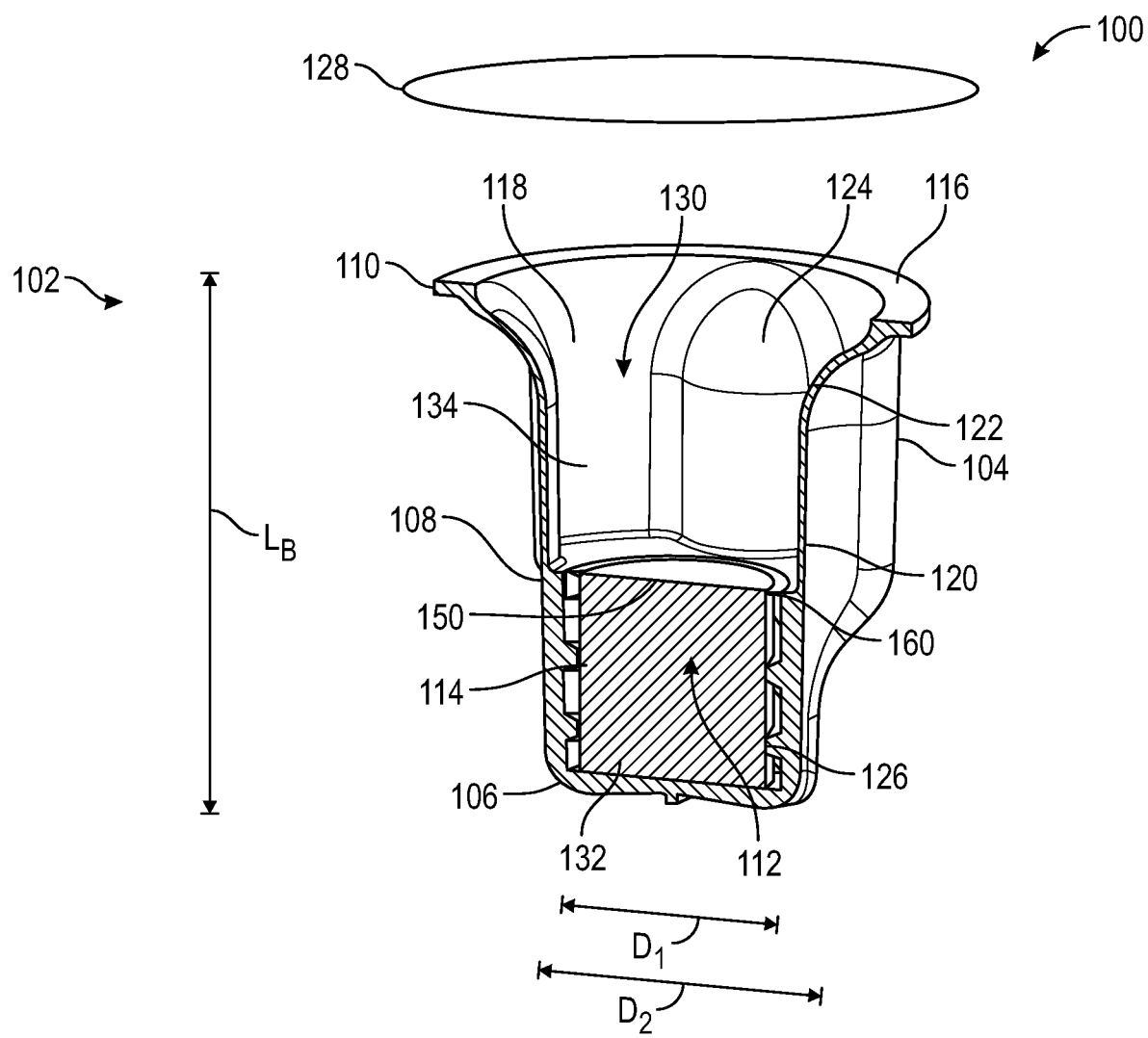
FIG. 3 shows a partial sectional view of a device according to an embodiment of the present disclosure.
Figure 9:
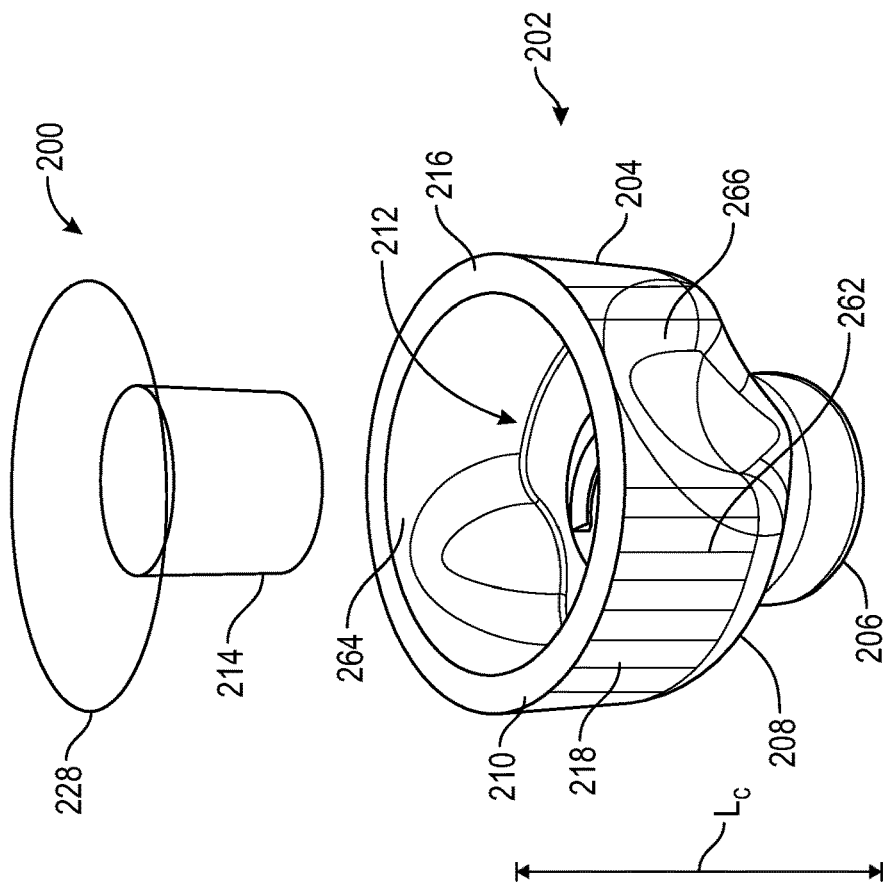
FIG. 9 shows a top perspective elevation view of an embodiment of a device of the present disclosure.
Figure 10:
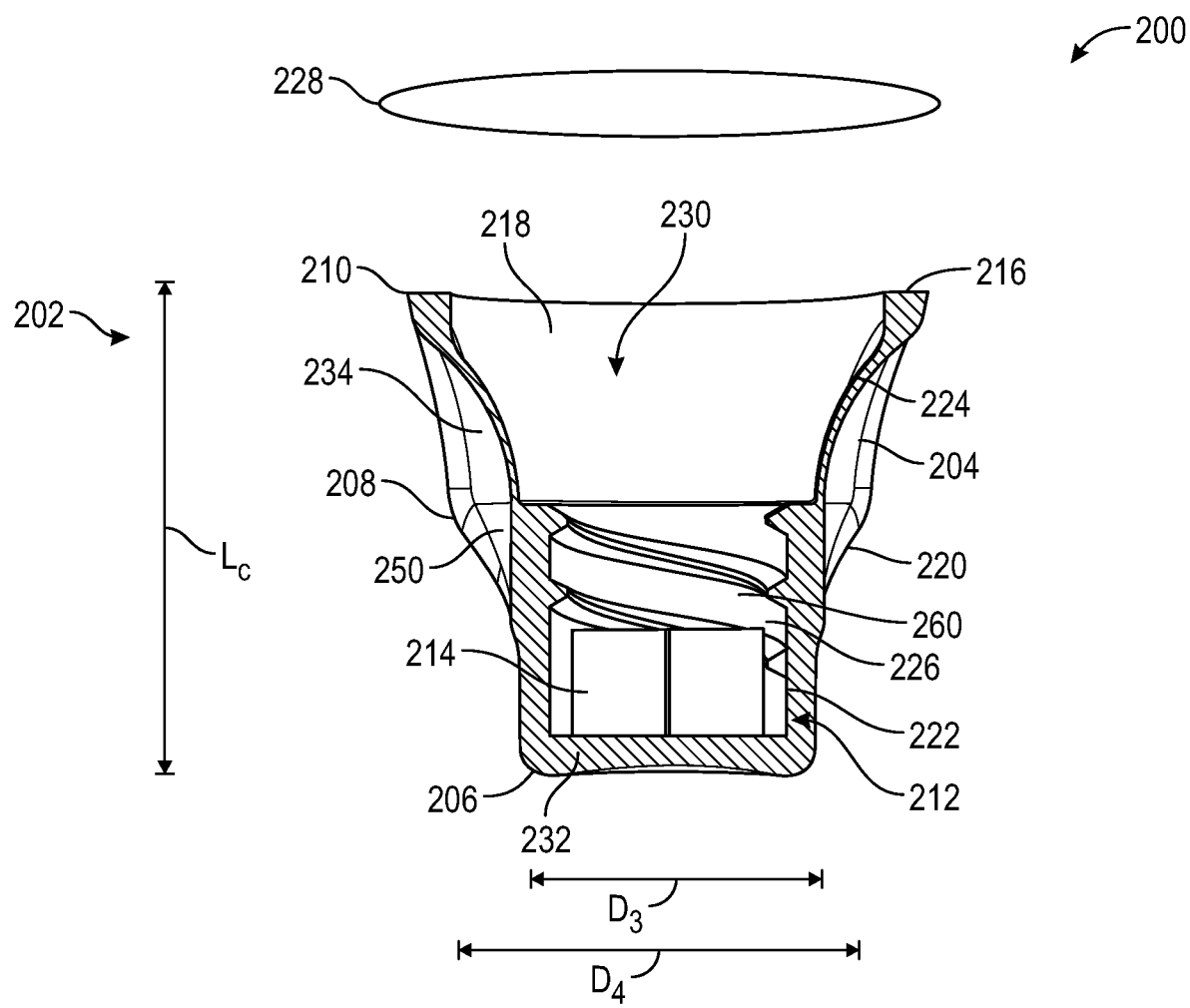
FIG. 10 shows a partial sectional view of a device according to an embodiment of the present disclosure.

The assembled device 100 according to one embodiment is shown in FIGS. 1-3. FIGS. 4-7 show the device engaged with medical connectors according to embodiments of the present disclosure. The assembled device 200 according to a second embodiment is shown in FIGS. 8-10. FIGS. 11-14 show the device of the second embodiment engaged with medical connectors according to embodiments of the present disclosure. FIGS. 15-18 show various medical connectors according to the prior art. Referring to FIGS. 1-3, device 100 for connection to a medical connector according to an exemplary embodiment of the present disclosure generally comprises a cap 102, absorbent material 114, a disinfectant or an antimicrobial agent, and a peelable seal 128. The cap 102 comprises an integral body 104, a closed end 106, an annular wall 108 having a length $L_B$ extending from the closed end 106 to an open end 110 that defines a chamber 112 containing an absorbent material 114 and disinfectant or antimicrobial agent. The open end 110 defines an end face 116 and an engagement surface 118.

Referring to FIG. 3, the annular wall 108 of the cap 102 comprises an exterior wall surface 120 and an interior wall surface 122. The interior wall surface 122 comprises a plurality of inwardly extending protrusions 124 sized and shaped to frictionally engage a male luer connector or a female luer connector with a compatible diameter. The interior wall surface 122 also comprises internal threads 126 adjacent the closed end 106. The internal threads 126 are adapted and sized to engage a female luer connector. The interior wall surface 122 defines an opening 150 adjacent the open end.

In one or more embodiments, the plurality of inwardly extending protrusions 124 is sized to define an opening 130 having a diameter that is dilatable. The dilatable opening 130 can be sized to frictionally engage a male luer connector or a female luer connector with a compatible diameter. In one or more embodiments, the dilatable opening 130 has a diameter that is dilatable from an initial diameter of from about 7-9 mm to a dilated diameter of about 9-12 mm to accept a collar of a male connector.

The peelable seal 128 is disposed on the end face 116 of the cap 102 to prevent the disinfectant or the antimicrobial agent from exiting the chamber 112.

Referring to FIGS. 1 and 2, in one or more embodiments, the exterior wall surface 122 of the cap 102 comprises a plurality of grip members 162.

The cap 102 comprises an annular cap wall 108 having a cap wall length $L_B$ extending from a cap closed end 106 to a cap open end 110. The cap 102 comprises an interior cap surface 164 and an exterior cap surface 166.

The peelable seal 128 is disposed on the cap open end 110 to prevent the disinfectant or the antimicrobial agent from exiting the chamber.

Figure 4:
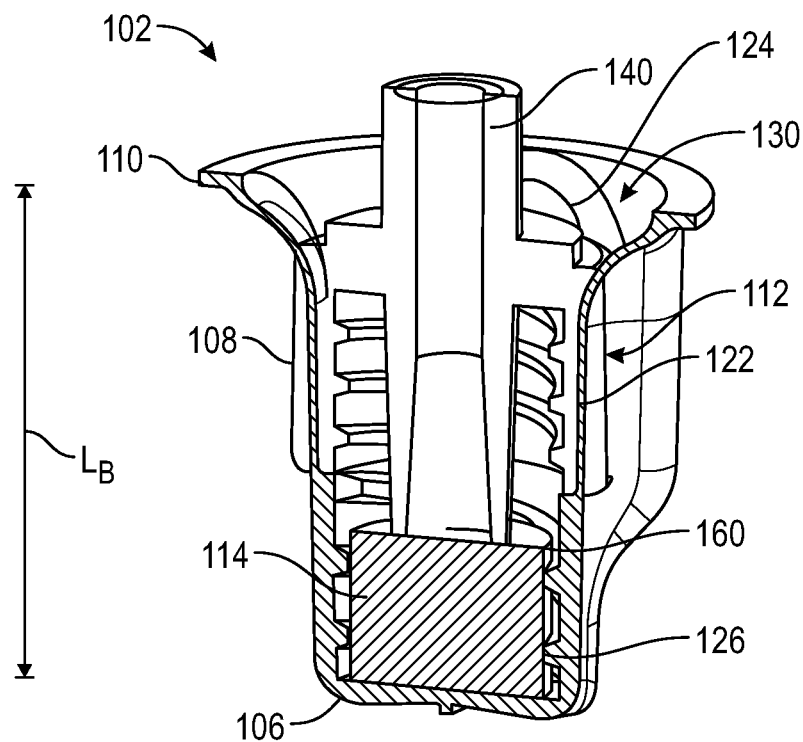
FIG. 4 shows a partial sectional view showing connection of the device of FIG. 1 to a male connector.

Referring to FIG. 4, in one or more embodiments, the male luer connector 140 frictionally engages the inwardly extending protrusions 124 via a press-fit connection upon insertion into the chamber 112. To limit inadvertent movement of the male luer connector 140, the plurality of inwardly extending protrusions 124 interferingly engage the male luer connector 140 in limiting movement thereof. With sufficient force being applied to the plurality of inwardly extending protrusions 124 by a male luer connector 140 when the male luer connector 140 is inserted into the open end 110 of the cap 102, the plurality of inwardly extending protrusions 124 may be caused to deform or be displaced around the male luer connector 140 so as to nest the male luer connector 140 and thereby restrict movement of the male luer connector 140. With sufficient force being applied to the plurality of inwardly extending protrusions 124 by a male luer connector 140 when the male luer connector 140 is inserted into the open end 110 of the cap 102, the plurality of inwardly extending protrusions 124 may be deformed to envelope the male luer connector 140 so as to nest the male luer connector 140 and thereby restrict movement of the male luer connector 140. In one or more embodiments, the plurality of inwardly extending protrusions 124 comprises 1-100 inwardly extending protrusions. In a specific embodiment, the plurality of inwardly extending protrusions 124 comprises 1-20 inwardly extending protrusions. In one or more embodiments, the plurality of inwardly extending protrusions 124 extends along an entire length of the interior wall surface 122 of the cap 102. In yet another embodiment, the plurality of inwardly extending protrusions 124 partially extends along the length of the interior wall surface 122 of the cap 102.

In one or more embodiments, the plurality of inwardly extending protrusions 124 is elongated. In one or more embodiments, the plurality of inwardly extending protrusions 124 is tapered.

In one or more embodiments, the cap 102 further includes a peripheral ledge 160 extending radially inward from the annular wall 108 which the male connector contacts when the male luer connector is inserted into the chamber 112.

In one or more embodiments, the opening adjacent to the open end 110 of the interior wall surface 122 is sized and adapted to receive a male luer connector in a press-fit connection.

Figure 5:
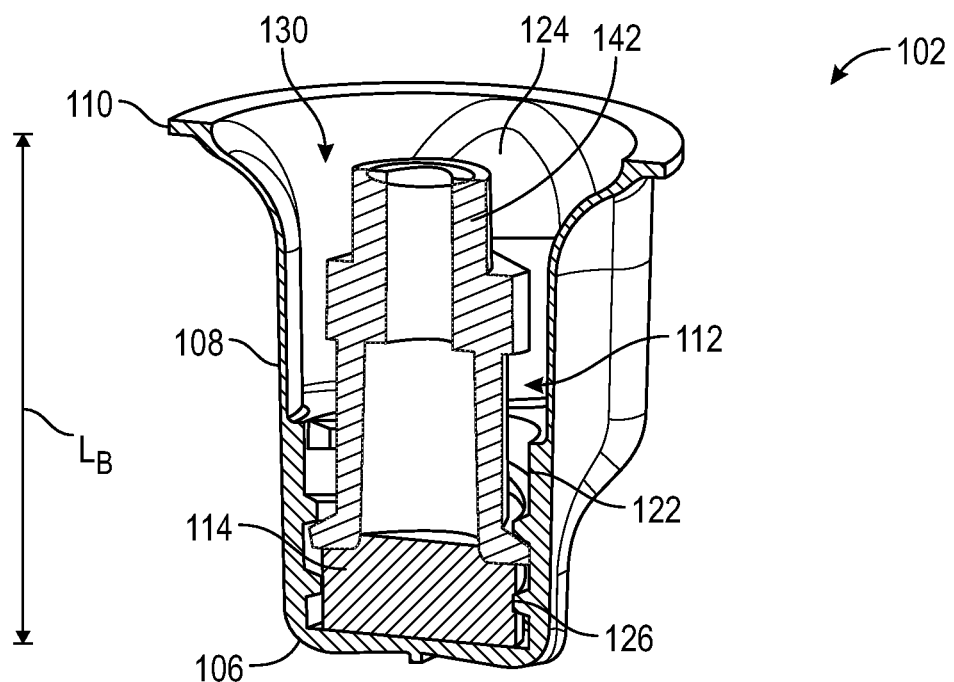
FIG. 5 shows a partial sectional view showing connection of the device of FIG. 1 to a female Luer stopcock.
Figure 6:
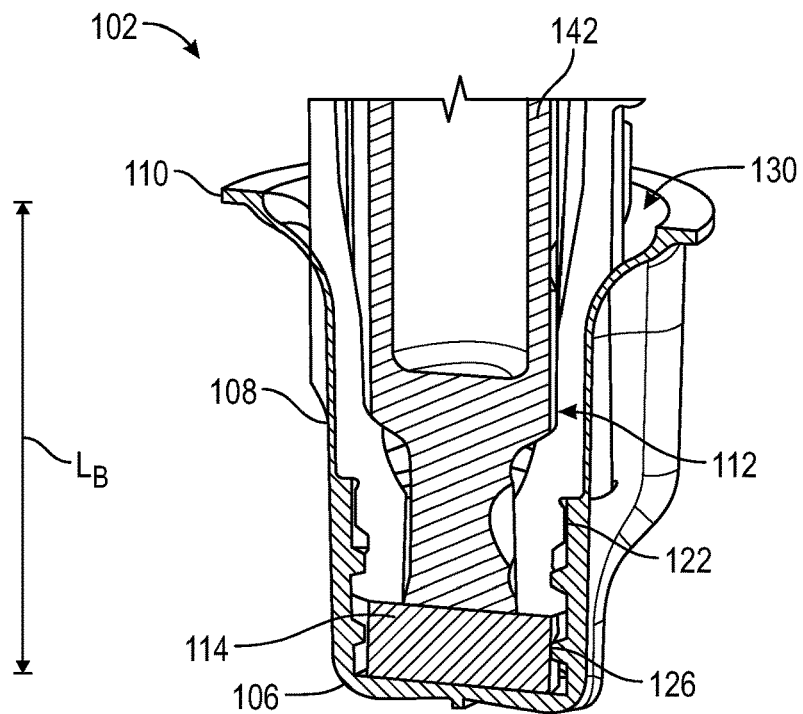
FIG. 6 shows a partial sectional view showing connection of the device of FIG. 1 to a female Luer MaxZero® connector.

Referring to FIGS. 4-6, the interior wall surface 122 comprises internal threads 126 adjacent to the closed end 106. The internal threads 126 are adapted and sized to engage a female luer connector. In one or more embodiments, the internal threads 126 adjacent the closed end 106 of the cap 102 partially extend along a length of the interior wall surface 122 of the cap 102.

The absorbent material 114 and the disinfectant or the antimicrobial agent contacts the male luer connector 140, the female luer connector 142, and the hemodialysis connector 144 after insertion of the connector through the dilatable opening 130.

Referring to FIGS. 5 and 6, the interior wall surface 122 comprises internal threads 126 adjacent to the closed end 106. The internal threads 126 are adapted and sized to engage a female luer connector 142. The absorbent material 114 and the disinfectant or the antimicrobial agent contacts the female luer connector 142 after insertion of the connector into the open end 110 of the cap 102.

In one or more embodiments, the female connector 142 may be selected from the group consisting essentially of needle-free connectors (or needleless connectors), catheter luer connectors, stopcocks, and hemodialysis connectors. In one or more embodiments, the female luer is selected from needleless connectors/needle-free connectors. In one or more embodiments, the needleless connector is selected from a Q-Syte connector, MaxPlus, MaxPlus Clear, MaxZero, UltraSite, Caresite, InVision-Plus, Safeline, One-Link, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector 140 may be an intravenous tubing end, stopcock or male lock luer.

Referring to FIG. 4, in one or more embodiments, the male luer connector 140 rests on the peripheral ledge 160 upon being fully inserted in into the chamber 112.

In one or more embodiments, the internal threads 126 adjacent the closed end 106 of the cap 102 partially extend along a length of the interior wall surface 122 of the cap.

In one or more embodiments, the male luer connector 140 frictionally engages the interior wall surface 122 via a press-fit connection upon insertion into the chamber 112.

In one or more embodiments, the opening 130 adjacent the open end 110 of the interior wall surface 122 of the cap is sized and adapted to receive a male luer connector 140 in a press-fit connection.

Figure 7:
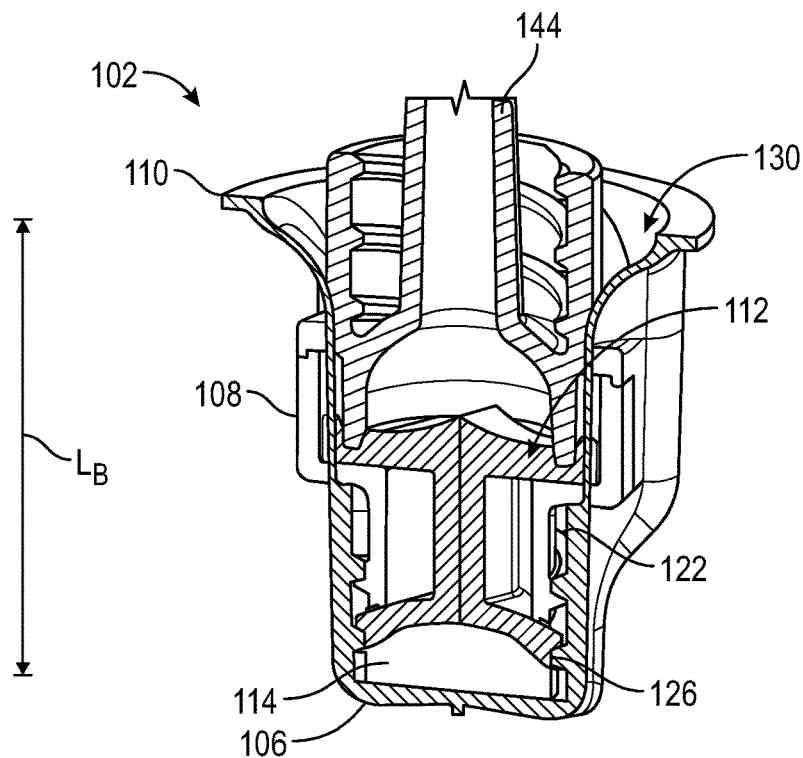
FIG. 7 shows a partial sectional view showing connection of the device of FIG. 1 to a Q-Syte® connector.
Figure 8:
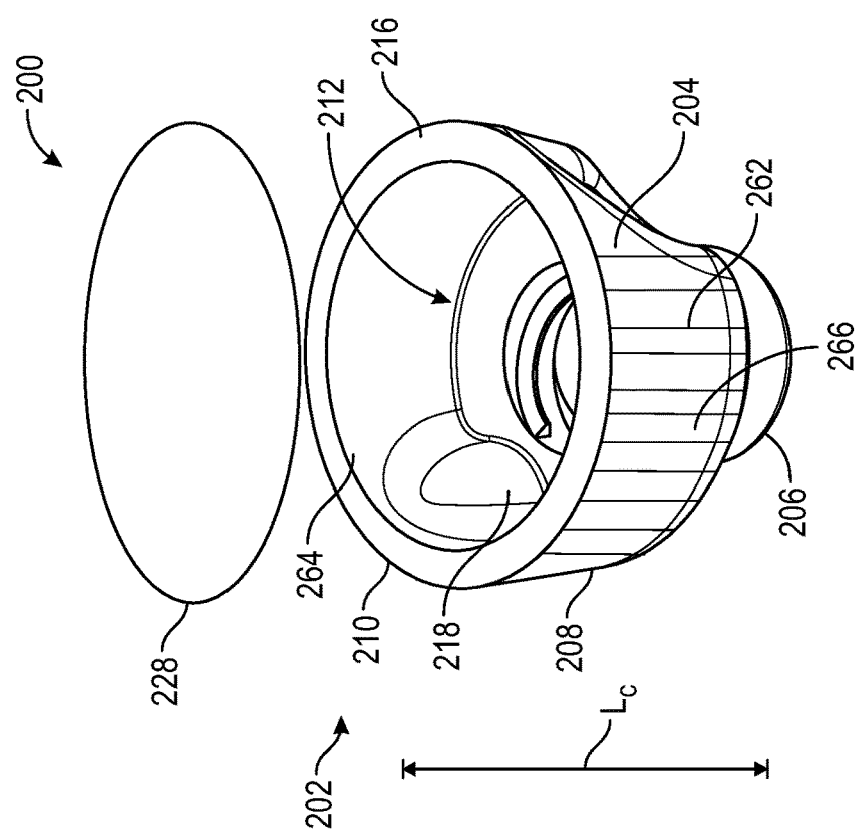
FIG. 8 shows a top perspective view of an embodiment of a device of the present disclosure.

Referring to FIG. 7, in one or more embodiments, the interior wall surface 122 comprises internal threads 126 adjacent to the closed end 106. The internal threads 126 are adapted and sized to engage a female connector or needleless connector 144. The absorbent material 114 and the disinfectant or the antimicrobial agent contacts the female connector or needleless connector 144 after insertion of the connector into the open end 110 of the cap 102.

In one or more embodiments, the closed female luer is selected from needleless connectors/needle-free connectors. In one or more embodiments, the needleless connector is selected from a Q-Syte connector, MaxPlus, MaxPlus Clear, MaxZero, UltraSite, Caresite, InVision-Plus, Safeline, One-Link, V-Link, ClearLink, NeutraClear, Clave, MicroClave, MicroClave Clear, Neutron, NanoClave, Kendall, Nexus, InVision, Vadsite, Bionector, etc.

Referring to FIG. 3, in one or more embodiments, the chamber 112 comprises a first portion 132 adjacent to the closed end 106 having a first portion diameter D1 and a second portion 134 adjacent the open end 110 having a second portion diameter D2, the first portion 132 and second portion 134 in fluid communication with each other, and the first portion diameter D1 being less than the second portion diameter D2.

In one or more embodiments, the annular wall 108 of the cap 102 is frusto-conically shaped.

Cap 102 is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap comprises a polypropylene or polyethylene material. In one or more embodiments, the exterior cap surface includes a plurality of grip members.

The assembled device 200 according to a second embodiment is shown in FIGS. 8-10. FIGS. 11-14 show the device 200 of the second embodiment engaged with medical connectors according to embodiments of the present disclosure. Referring to FIGS. 8-10, device 200 for connection to a medical connector according to an exemplary embodiment of the present disclosure generally comprises a cap 202, absorbent material 214, a disinfectant or an antimicrobial agent, and a peelable seal 228. The cap 202 comprises an integral body 204, a closed end 206, an annular wall 208 having a length $L_C$ extending from the closed end 206 to an open end 210 that defines a chamber 212 containing an absorbent material 214 and disinfectant or antimicrobial agent. The open end 210 defines an end face 216 and an engagement surface 218. In one or more embodiments, the length $L_C$ of cap 202 is shorter than/less than the length $L_B$ of the cap 102.

Referring to FIG. 10, the annular wall 208 of the cap 202 comprises an exterior wall surface 220 and an interior wall surface 222. The interior wall surface 222 comprises a plurality of inwardly extending protrusions 224 sized and shaped to frictionally engage a male luer connector. In one or more embodiments, a female luer connector having a very large diameter and short length, such as a Q-Syte® in particular can also engage with the protrusion through interference/frictional fit.

The interior wall surface 222 also comprises internal threads 226 adjacent the closed end 206. The internal threads 226 are adapted and sized to engage a female luer connector. The interior wall surface 222 defines an opening 250 adjacent the open end 210.

In one or more embodiments, the plurality of inwardly extending protrusions 224 is sized to define an opening 130 having a diameter that is dilatable. The dilatable opening 130 can be sized to frictionally engage a male luer connector. In one or more embodiments, the dilatable opening 130 has a diameter that is dilatable from an initial diameter of from about 7-9 mm to a dilated diameter of about 9-12 mm to accept a collar of a male connector. In one or more embodiments, a female luer connector having a very large diameter and short length, such as a Q-Syte® in particular can also engage with the protrusion through interference/frictional fit.

The peelable seal 228 is disposed on the end face 216 of the cap 202 to prevent the disinfectant or the antimicrobial agent from exiting the chamber 212.

Referring to FIGS. 8 and 9, in one or more embodiments, the exterior wall surface 222 of the cap 202 comprises a plurality of grip members 262.

The cap 202 comprises an annular cap wall 208 having a cap wall length $L_C$ extending from a cap closed end 206 to a cap open end 210. In one or more embodiments, the cap wall length $L_C$ of cap 202 is shorter than/less than the cap wall length $L_B$ of cap 102. The cap 202 comprises an interior cap surface 264 and an exterior cap surface 266.

The peelable seal 228 is disposed on the cap open end 210 to prevent the disinfectant or the antimicrobial agent from exiting the chamber.

Figure 11:
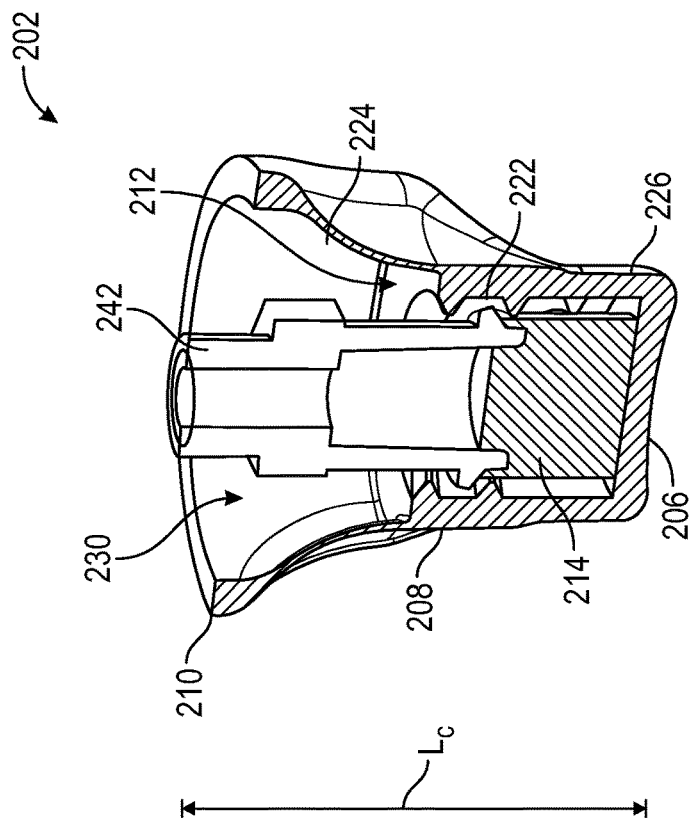
FIG. 11 shows a partial sectional view showing connection of the device of FIG. 8 to a male connector.

Referring to FIG. 11, in one or more embodiments, the male luer connector 240 frictionally engages the inwardly extending protrusions 224 via a press-fit connection upon insertion into the chamber 212. To limit inadvertent movement of the male luer connector 240, the plurality of inwardly extending protrusions 224 interferingly engage the male luer connector 240 in limiting movement thereof. With sufficient force being applied to the plurality of inwardly extending protrusions 224 by a male luer connector 240 when the male luer connector 240 is inserted into the open end 210 of the cap 202, the plurality of inwardly extending protrusions 224 may be caused to deform or be displaced around the male luer connector 240 so as to nest the male luer connector 240 and thereby restrict movement of the male luer connector 240. With sufficient force being applied to the plurality of inwardly extending protrusions 224 by a male luer connector 240 when the male luer connector 240 is inserted into the open end 210 of the cap 202, the plurality of inwardly extending protrusions 224 may be deformed to envelope the male luer connector 240 so as to nest the male luer connector 240 and thereby restrict movement of the male luer connector 240. In one or more embodiments, the plurality of inwardly extending protrusions 224 comprises 1-100 inwardly extending protrusions. In a specific embodiment, the plurality of inwardly extending protrusions 224 comprises 1-20 inwardly extending protrusions. In one or more embodiments, the plurality of inwardly extending protrusions 224 extends along an entire length of the interior wall surface 222 of the cap 202. In yet another embodiment, the plurality of inwardly extending protrusions 224 partially extends along the length of the interior wall surface 222 of the cap 202. In one or more embodiments, a female luer connector having a very large diameter and short length, such as a Q-Syte® in particular can also engage with the protrusion through interference/frictional fit.

In one or more embodiments, the plurality of inwardly extending protrusions 224 is elongated. In one or more embodiments, the plurality of inwardly extending protrusions 224 is tapered.

In one or more embodiments, the cap 202 further includes a peripheral ledge 260 extending radially inward from the annular wall 208 which the male connector contacts when the male luer connector is inserted into the chamber 212.

In one or more embodiments, the opening adjacent the open end 210 of the interior wall surface 222 is sized and adapted to receive a male luer connector in a press-fit connection.

Figure 12:
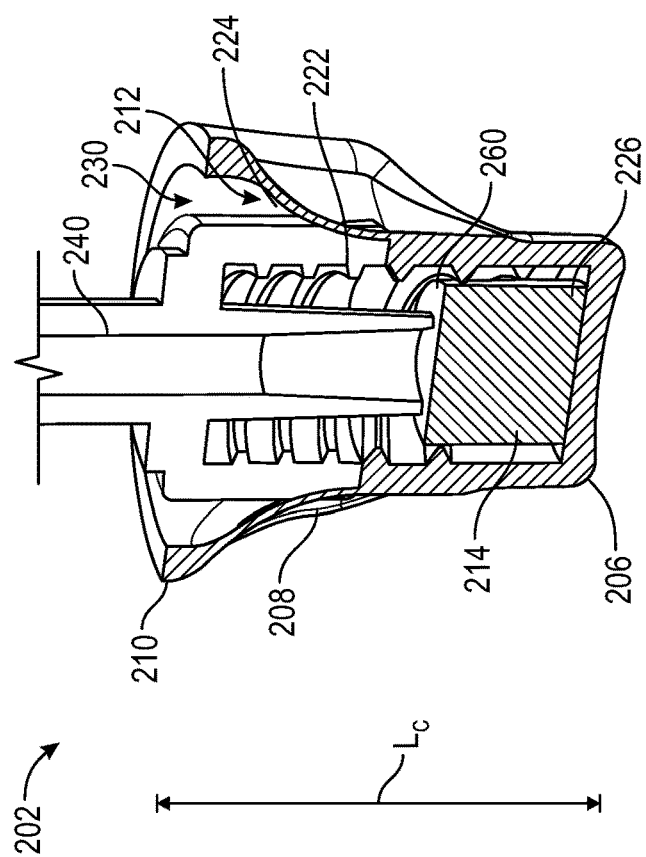
FIG. 12 shows a partial sectional view showing connection of the device of FIG. 8 to a female Luer stopcock.
Figure 13:
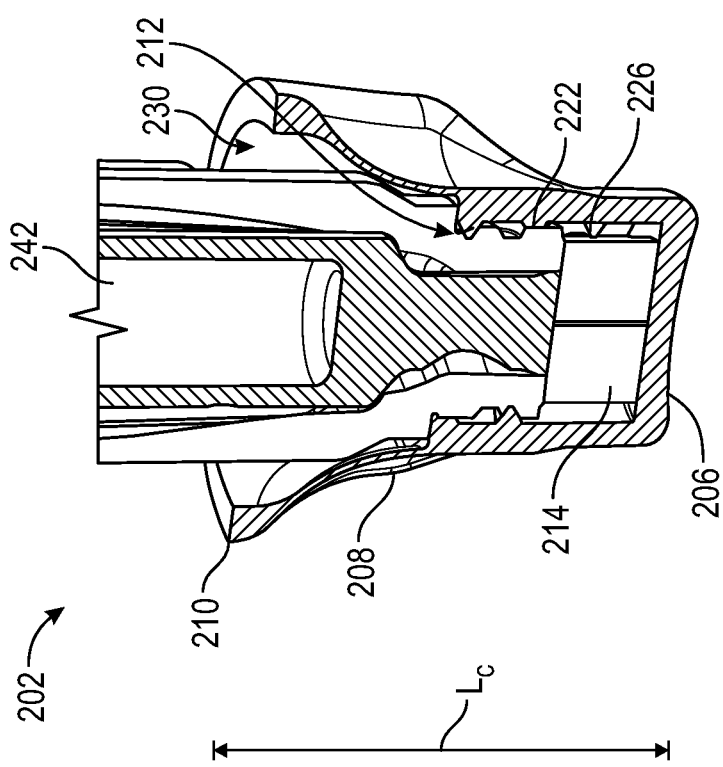
FIG. 13 shows a partial sectional view showing connection of the device of FIG. 8 to a female Luer MaxZero.
Figure 15:
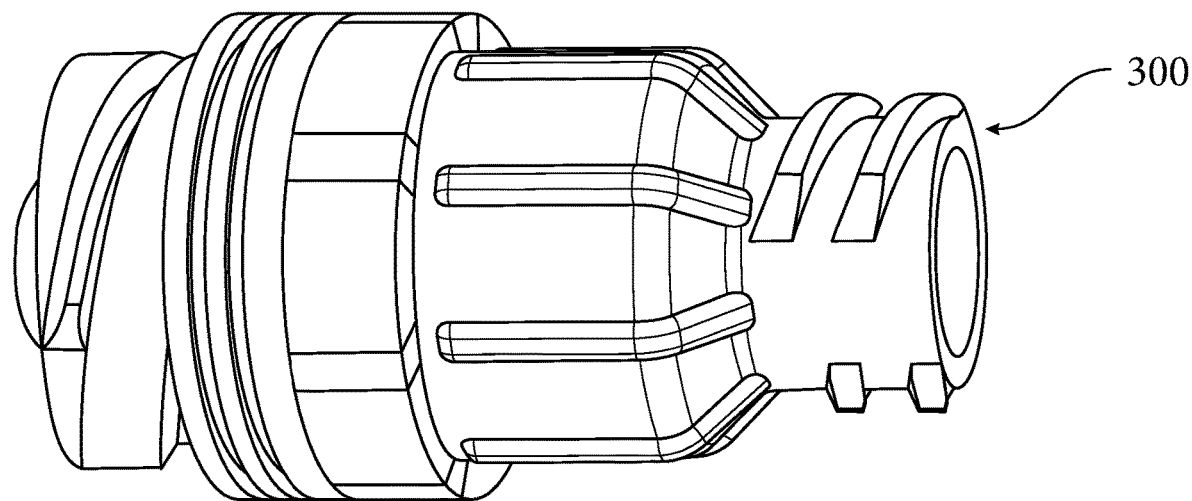
FIG. 15 shows a perspective view of a female luer connector with septum according to the prior art.
Figure 16:
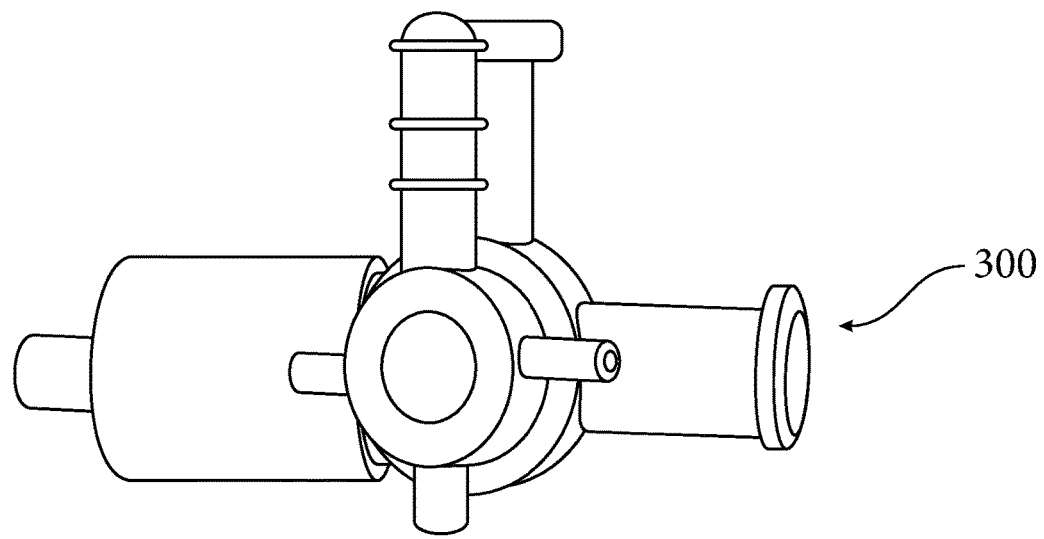
FIG. 16 shows a perspective view a female luer connector with stopcock according to the prior art.
Figure 17:
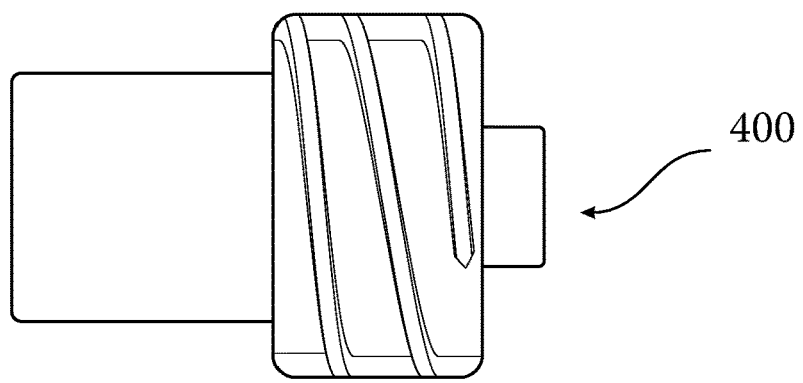
FIG. 17 shows a perspective view of a male luer connector according to the prior art.
Figure 18:
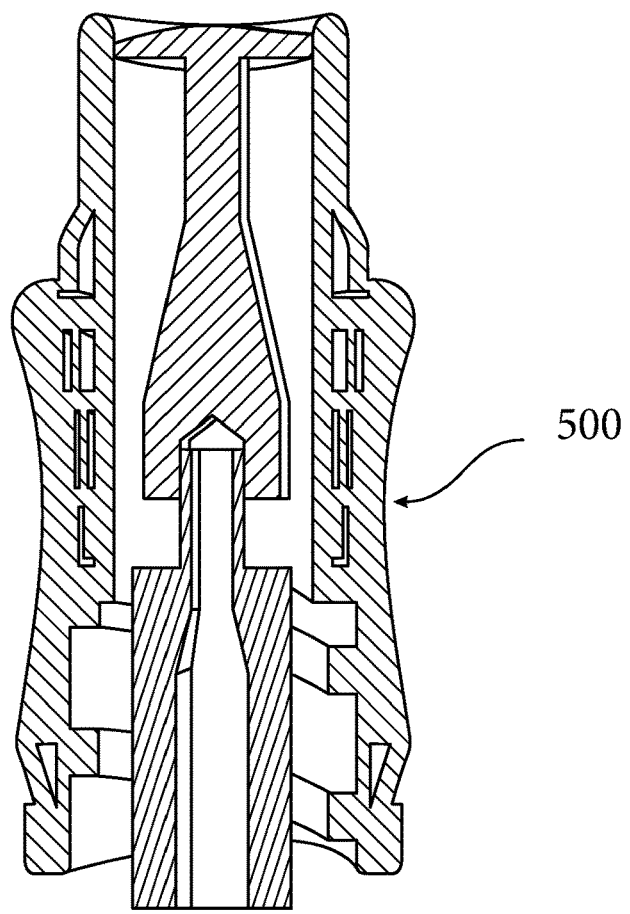
FIG. 18 shows a perspective view of a hemodialysis connector according to the prior art.

Referring to FIGS. 11-13, the interior wall surface 222 comprises internal threads 226 adjacent to the closed end 206. The internal threads 226 are adapted and sized to engage a female luer connector 242. In one or more embodiments, the internal threads 226 adjacent the closed end 206 of the cap 202 partially extend along a length of the interior wall surface 222 of the cap 202.

The absorbent material 214 and the disinfectant or the antimicrobial agent contacts the male luer connector 240, the female luer connector 242, and the hemodialysis connector 244 after insertion of the connector through the dilatable opening 230.

Referring to FIGS. 12 and 13, the interior wall surface 222 comprises internal threads 226 adjacent to the closed end 206. The internal threads 226 are adapted and sized to engage a female luer connector 242. The absorbent material 214 and the disinfectant or the antimicrobial agent contacts the female luer connector 242 after insertion of the connector into the open end 210 of the cap 202.

In one or more embodiments, the female connector 142 may be selected from the group consisting essentially of needle-free connectors, catheter luer connectors, stopcocks, and hemodialysis connectors.

In one or more embodiments, the male connector 240 may be an intravenous tubing end, stopcock or male lock luer.

Referring to FIG. 11, in one or more embodiments, the male luer connector 240 rests on the peripheral ledge 260 upon being fully inserted in into the chamber 212.

In one or more embodiments, the internal threads 226 adjacent the closed end 206 of the cap 202 partially extend along a length of the interior wall surface 222 of the cap.

In one or more embodiments, the male luer connector 240 frictionally engages the interior wall surface 222 via a press-fit connection upon insertion into the chamber 212.

In one or more embodiments, the opening 230 adjacent the open end 210 of the interior wall surface 222 of the cap is sized and adapted to receive a male luer connector 240 in a press-fit connection.

Figure 14:
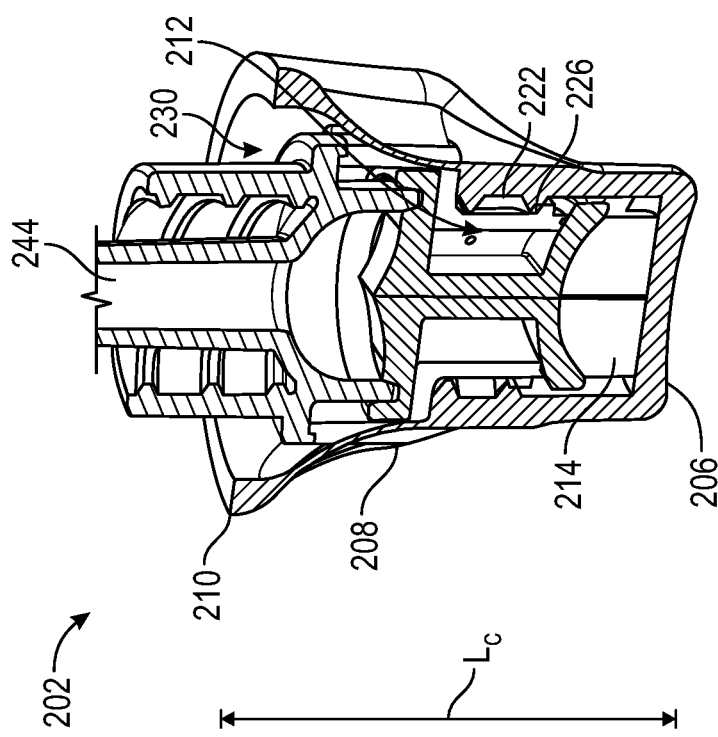
FIG. 14 shows a partial sectional view showing connection of the device of FIG. 8 to a Q-Syte connector.

Referring to FIG. 14, in one or more embodiments, the interior wall surface 222 comprises internal threads 226 adjacent to the closed end 206. The internal threads 226 are adapted and sized to engage a female connector or a needleless connector 244. The absorbent material 214 and the disinfectant or the antimicrobial agent contacts the female connector or needleless connector 244 after insertion of the connector into the open end 210 of the cap 202.

In one or more embodiments, the closed female luer is selected from needleless connectors/needle-free connectors. In one or more embodiments, the needleless connector 224 is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

Referring to FIG. 10, in one or more embodiments, the chamber 212 comprises a first portion 232 adjacent the closed end 206 having a first portion diameter D3 and a second portion 234 adjacent the open end 210 having a second portion diameter D4, the first portion 232 and second portion 234 in fluid communication with each other and the first portion diameter D3 being less than the second portion diameter D4.

In one or more embodiments, the annular wall 208 of the cap 202 is frusto-conically shaped.

Cap 202 is made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap 202 comprises a polypropylene or polyethylene material. In one or more embodiments, the exterior cap surface 266 includes a plurality of grip members 262.

Referring to FIGS. 1-7, in one or more embodiments, the absorbent material 114 is under radial compression by the internal threads 126 to retain the absorbent material 114 in the chamber. In one or more embodiments, the absorbent material is retained in the chamber without radial compression by the internal threads. In one or more embodiments, the absorbent material 114 is a foam or a sponge. In a specific embodiment, the foam is a polyurethane foam. In a specific embodiment the absorbent material 114 is in the form of a foam plug.

The device 100 can achieve disinfection when used on luer connectors by integrating disinfectant or antimicrobial agent in the chamber 112 of the cap 102. The disinfectant or antimicrobial agent can be directly included in the chamber 112 or disinfectant or antimicrobial agent can be absorbed into sponges or foam material that fills the chamber 112 of the cap 102. The device 100 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 114 toward the closed end 106 of the chamber 112 upon connection to the female luer connector 142 or the male luer connector 140 or the needleless connector 144 allows the connector to contact the disinfectant or antimicrobial agent to disinfect the female luer connector 142 or the male luer connector 140 or the needleless connector 144.

The peelable seal 128 on the end face 116 to prevent the disinfectant or the antimicrobial agent from exiting the chamber. In one or embodiments, the peelable seal 128 may be placed on the end face 116 to prevent the disinfectant or the antimicrobial agent from exiting the chamber 112.

In one or more embodiments, the peelable seal 128 comprises an aluminum or multi-layer polymer film peel back top. In a specific embodiment, the peelable seal 128 is heat-sealed or induction sealed to the engagement surface 118 on the cap open end 110. In one or more embodiments, the peelable seal 128 comprises a moisture barrier.

In one or more embodiments, the cap exterior wall surface 166 includes a plurality of grip members 162.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, cap 102 engages with male luer connectors 140 and also with female luer connectors 142, hemodialysis connector, and with needleless connectors 144, thereby allowing the user to clean different types of connectors with a single device. Upon mounting the cap 102 onto female luer connectors 142, the female luer connector 142 is inserted into the chamber 112 and screwed onto the internal threads 126 of the cap. Upon mounting the cap 102 onto a male luer connector 140, the male luer connector 140 frictionally engages the inwardly extending protrusions 124 on the interior wall surface 122 upon insertion into the chamber 112. In one or more embodiments, a female luer connector having a very large diameter and short length, such as a Q-Syte® in particular can also engage with the protrusion through interference/frictional fit. Hence, the device 100 of the present disclosure can be mounted onto both male and female luer connectors thus fulfilling a current need in the art.

Referring to FIGS. 8-14, in one or more embodiments, the absorbent material 214 is under radial compression by the internal threads 226 to retain the absorbent material 214 in the chamber. In one or more embodiments, the absorbent material is retained in the chamber without radial compression by the internal threads. In one or more embodiments, the absorbent material 214 is a foam or a sponge. In a specific embodiment, the foam is a polyurethane foam. In a specific embodiment the absorbent material 214 is in the form of a foam plug.

The device 200 can achieve disinfection when used on luer connectors by integrating disinfectant or antimicrobial agent in the chamber 212 of the cap 202. The disinfectant or antimicrobial agent can be directly included in the chamber 212 or disinfectant or antimicrobial agent can be absorbed into sponges or foam material that fills the chamber 212 of the cap 202. The device 200 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 214 toward the closed end 106 of the chamber 212 upon connection to the female luer connector 242 or the male luer connector 140 or the needleless connector 244 allows the connector to contact the disinfectant or antimicrobial agent to disinfect the female luer connector 242 or the male luer connector 240 or the needleless connector 244.

The peelable seal 228 on the end face 216 to prevent the disinfectant or the antimicrobial agent from exiting the chamber. In one or embodiments, the peelable seal 228 may be placed on the end face 216 to prevent the disinfectant or the antimicrobial agent from exiting the chamber 212.

In one or more embodiments, the peelable seal 228 comprises an aluminum or multi-layer polymer film peel back top. In a specific embodiment, the peelable seal 228 is heat-sealed or induction sealed to the engagement surface 218 on the cap open end 210. In one or more embodiments, the peelable seal 228 comprises a moisture barrier.

In one or more embodiments, the cap exterior wall surface 266 includes a plurality of grip members 262.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, cap 202 engages with male luer connectors 240 and also with female luer connectors 242 and with needleless connectors 244, thereby allowing the user to clean different types of connectors with a single device. Upon mounting the cap 202 onto female luer connectors 242, the female luer connector 242 is inserted into the chamber 212 and screwed onto the internal threads 226 of the cap. Upon mounting the cap 202 onto a male luer connector 240, the male luer connector 240 frictionally engages the inwardly extending protrusions 224 on the interior wall surface 222 upon insertion into the chamber 212. Hence, the device 200 of the present disclosure can be mounted onto both male and female luer connectors thus fulfilling a current need in the art.

Referring to FIGS. 15 to 18, in one or more embodiments, the cap of the device of the present disclosure may form a fluid-tight seal with a female luer connector 300, a male luer connector 400 or hemodialysis connector 500. Referring to FIGS. 15 to 18, in one or more embodiments, the cap of the device of the present disclosure is tapered to form a fluid-tight seal with a male luer connector 400. In specific embodiments, the cap is compliant with ISO standards (e.g., ISO 594-1:1986 and ISO 594-2:1998) for forming a seal with a male luer connector.

In one or more embodiments, the cap of the device of the present disclosure has threads that have a size and pitch to engage a threadable segment of a female connector, such as for example, a female luer connector. Such connectors are generally and commonly used as catheter and other fluid-tight protective connectors in medical applications. In some embodiments, the cap provides a protective cover for a female luer connector when engaged with the connector when threads from the female luer connector engage and form a releasable connection with threads of the cap.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

In one or more embodiments, threads of the cap are sized and pitched to engage threads of a male luer-lock connector. For example, connector can comprise the end of an IV tubing set that is disconnected from an IV catheter needleless injection site.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber or engaging the internal threads, such that the medical connector contacts the absorbent material and the disinfectant or antimicrobial agent.

In one or more embodiments, an assembly comprises the device of one or more embodiments connected to a medical connector. In one or more embodiments, the medical connector is selected from a male luer connector, a female luer connector, and a needleless connector.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A device for connection to a medical connector, the device comprising:
    a cap comprising an integral body, a closed end, an annular wall having a length extending from the closed end to an open end and defining a chamber containing an absorbent material and either disinfectant or antimicrobial agent, the open end defining an end face, and defining an engagement surface;
    the annular wall having an exterior wall surface and an interior wall surface;
    a plurality of inwardly extending, discrete elongated protrusions adjacent to the open end and at least partially extending longitudinally along a length of the interior wall surface to frictionally engage a male luer connector in a press-fit connection, a portion of each of the inwardly extending, discrete elongated protrusions respectively having: a major axis that is axially aligned with a centerline of the chamber of the cap, a minor axis that is perpendicular to the major axis, and a convex-curved, cross-sectional profile along the minor axis whose apex is aligned with the major axis, the major axes of each of the inwardly extending, discrete elongated protrusions symmetrically spaced about a circumference of the annular wall, so that a central axis of the male luer connector inserted within the chamber aligns with the centerline of the chamber, deforming the convex-curved cross-sectional profile of each of the inwardly extending, discrete elongated protrusions;
    the interior wall surface comprising internal threads adjacent the closed end and extending from the closed end partially along a length of the interior wall surface towards the plurality of inwardly extending, discrete elongated protrusions, the internal threads adapted and sized to engage corresponding threads of a female luer connector; and
    a peelable seal on the end face to prevent the disinfectant or the antimicrobial agent from exiting the chamber.

2. The device of claim 1, wherein the plurality of inwardly extending, discrete elongated protrusions are sized to define an opening having a diameter that is deformable from an initial diameter of from about 7-9 mm to a second diameter of about 9-12 mm to frictionally engage a collar of a male connector in a press-fit connection.

3. The device of claim 1, wherein the male luer connector frictionally engages the plurality of inwardly extending, discrete elongated protrusions via a press-fit connection upon insertion into the chamber.

4. The device of claim 1, wherein the cap comprises a polypropylene or polyethylene material.

5. The device of claim 1, wherein the chamber comprises a first portion adjacent the closed end having a first portion diameter D1 and a second portion adjacent the open end having a second portion diameter D2, the first portion and second portion in fluid communication with each other and the first portion diameter being less than the second portion diameter.

6. The device of claim 1, wherein the annular wall of the cap is frusto-conically shaped.

7. The device of claim 1, wherein the absorbent material is a foam.

8. The device of claim 7, wherein the foam is a polyurethane foam.

9. The device of claim 1, wherein the absorbent material compresses toward the closed end of the chamber upon connection to the female luer connector or the male luer connector.

10. The device of claim 9, wherein compression of the absorbent material disinfects the female luer connector or the male luer connector.

11. The device of claim 1, wherein the absorbent material is under radial compression by the internal threads to retain the absorbent material in the chamber.

12. The device of claim 1, wherein the disinfectant or antimicrobial agent is selected from a group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

13. The device of claim 12, wherein the disinfectant or antimicrobial agent comprises at least one of chlorhexidine gluconate and chlorhexidine diacetate.

14. The device of claim 1, wherein the peelable seal comprises an aluminum or multi-layer polymer film peel back top.

15. The device of claim 1, wherein the peelable seal is heat-sealed or induction sealed to the engagement surface.

16. The device of claim 1, wherein the cap further comprises a peripheral ledge extending radially inward from the annular wall, wherein the male luer connector rests on the peripheral ledge upon being fully inserted into the chamber.

17. The device of claim 1, wherein the plurality of inwardly extending, discrete elongated protrusions are deformable.

18. The device of claim 1, wherein the plurality of inwardly extending, discrete elongated protrusions extend along an entire length of the interior wall surface of the cap.

* * * * *